US012797095B2

(12) United States Patent
Simmons

(10) Patent No.: US 12,797,095 B2
(45) Date of Patent: Nov. 17, 2026

(54) CLOT DISRUPTOR AND SYSTEMS AND METHODS OF USING SAME

(71) Applicants: United States Government as Represented by the Department of Veterans Affairs, Washington, DC (US); The Board Of Regents Of The University System Of Georgia By And On Behalf Of Augusta University, August, GA (US)

(72) Inventor: Matthew Simmons, Augusta, GA (US)

(73) Assignees: United States Government as represented by the Department of Veterans Affairs, Washington, DC (US); The Board Of Regents Of The University System Of Georgia By And On Behalf Of Augusta University, Augusta, GA (US)

( * ) Notice: Subject to any disclaimer, the term of this patent is extended or adjusted under 35 U.S.C. 154(b) by 433 days.

(21) Appl. No.: 18/309,054

(22) Filed: Apr. 28, 2023

(65) Prior Publication Data

US 2023/0346405 A1 Nov. 2, 2023

Related U.S. Application Data

(60) Provisional application No. 63/335,953, filed on Apr. 28, 2022.

(51) Int. Cl.
*A61B 17/221* (2006.01)
*A61B 17/22* (2006.01)

(52) U.S. Cl.
CPC .. *A61B 17/221* (2013.01); *A61B 2017/22079* (2013.01); *A61B 2017/2212* (2013.01)

(58) Field of Classification Search
CPC ............ A61B 17/221; A61B 17/32056; A61B 2017/22079; A61B 2017/2212; A61B 17/22; A61B 17/3205
See application file for complete search history.

(56) References Cited

U.S. PATENT DOCUMENTS 4,905,691 A * 3/1990 Rydell .................. A61B 18/14 606/47
6,015,381 A 1/2000 Ouchi
8,216,247 B2 * 7/2012 Kaneko ............ A61B 17/32056 606/113
8,480,670 B2 7/2013 Sugita
(Continued)

FOREIGN PATENT DOCUMENTS

CN 111214274 6/2020
JP 2007244783 9/2007
(Continued)

*Primary Examiner* — Tan-Uyen T Ho
*Assistant Examiner* — Osama Nemer
(74) *Attorney, Agent, or Firm* — Ballard Spahr LLP

(57) ABSTRACT

An apparatus has an outer sleeve having a longitudinal axis and a wire having opposed first and second ends. A portion of the wire forms a wire loop that extends from the opposed first and second ends in a first direction along the longitudinal axis. The wire loop surrounds an operational area. Retraction of at least one of the first and second ends of the wire in a second direction opposite the first direction along the longitudinal axis decreases the operational area of the wire loop.

18 Claims, 9 Drawing Sheets

(56) References Cited

U.S. PATENT DOCUMENTS

| | | | | |
|---|---|---|---|---|
| 10,835,270 | B2 * | 11/2020 | Saunders | A61B 17/221 |
| 11,241,249 | B2 | 2/2022 | Nakajima et al. | |
| 2004/0059352 | A1 * | 3/2004 | Burbank | A61B 17/0469 606/148 |
| 2006/0106281 | A1 * | 5/2006 | Boulais | A61B 90/98 600/101 |
| 2008/0243183 | A1 * | 10/2008 | Miller | A61B 17/0469 606/228 |
| 2012/0022558 | A1 * | 1/2012 | Friedman | A61B 17/12013 606/139 |
| 2013/0144311 | A1 * | 6/2013 | Fung | A61B 17/12013 606/139 |
| 2015/0119884 | A1 * | 4/2015 | Fung | A61B 18/1492 606/41 |
| 2016/0310144 | A1 * | 10/2016 | Kimura | A61B 17/12013 |
| 2017/0231647 | A1 * | 8/2017 | Saunders | A61B 17/221 606/113 |
| 2018/0333202 | A1 * | 11/2018 | Hancock | H01P 1/066 |
| 2019/0298382 | A1 * | 10/2019 | Fung | A61B 17/12013 |
| 2020/0093536 | A1 | 3/2020 | Hancock et al. | |

FOREIGN PATENT DOCUMENTS

| | | | |
|---|---|---|---|
| JP | 4297467 | B2 * | 7/2009 |
| JP | 4638683 | | 2/2011 |

* cited by examiner

CLOT DISRUPTOR AND SYSTEMS AND METHODS OF USING SAME

CROSS-REFERENCE TO RELATED APPLICATIONS

This application claims priority to and the benefit of the filing date of U.S. Provisional Application No. 63/335,935, filed Apr. 28, 2022, the entirety of which is hereby incorporated by reference herein.

FIELD

This disclosure relates to devices and methods for disrupting blood clots, such as, for example, blood clots in a bladder.

BACKGROUND

Severe hematuria due to surgery, bladder tumors, or other disease entities can result in the formation of blood clots within the bladder. These can result in blockage of the bladder outlet with subsequent obstruction. In most cases, the clots are large and can fill the entire bladder. Current management involves suctioning the clot through a 28 French (0.93 cm) cystoscope sheath. With the patient under anesthesia, the cystoscope is advanced through the urethra in a sheath and into the bladder. The cystoscope is removed and a manual suction bulb is then attached to the sheath. Extensive saline instillation and suctioning is then conducted. Fluid turbulence and suction forces act to fragment the clot, and the small pieces are removed piecemeal from the bladder. Clots that have been in the bladder for more than 24 hours are more resistant to fragmentation due to fibrinization. Cystoscopic suction-based clot evacuation can require over an hour for large clots and conveys the risk of bladder injury, systemic fluid overload and bladder perforation.

Thus, a need exists for a minimally invasive way to remove blood clots within the bladder.

SUMMARY

Disclosed herein, in one aspect, is an apparatus having an outer sleeve having a longitudinal axis and a wire having opposed first and second ends. A portion of the wire forms a wire loop that extends from the opposed first and second ends in a first direction along the longitudinal axis. The wire loop surrounds an operational area. Retraction of at least one of the first and second ends of the wire in a second direction opposite the first direction along the longitudinal axis decreases the operational area of the wire loop.

Additional advantages of the disclosed system and method will be set forth in part in the description which follows, and in part will be understood from the description, or may be learned by practice of the disclosed system and method. The advantages of the disclosed system and method will be realized and attained by means of the elements and combinations particularly pointed out in the appended claims. It is to be understood that both the foregoing general description and the following detailed description are exemplary and explanatory only and are not restrictive of the invention as claimed.

BRIEF DESCRIPTION OF THE DRAWINGS

The accompanying drawings, which are incorporated in and constitute a part of this specification, illustrate several embodiments of the disclosed apparatus, system, and method and together with the description, serve to explain the principles of the disclosed apparatus, system, and method.

DETAILED DESCRIPTION

Figure 2:
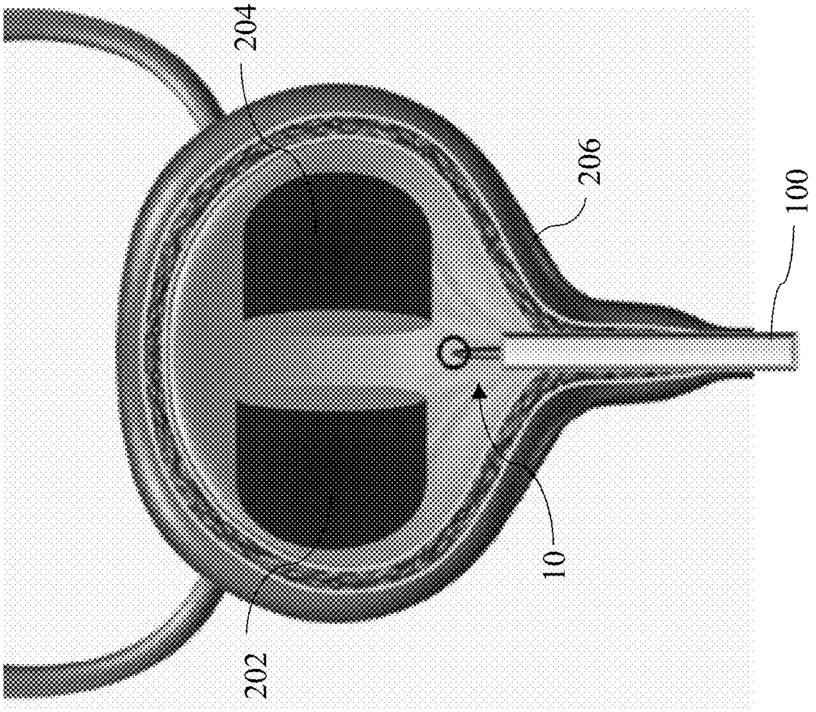
FIG. 2 is a schematic diagram of the apparatus of FIG. 1 having cut through the clot to divide the clot into smaller fragments.

The disclosed system and method may be understood more readily by reference to the following detailed description of particular embodiments and the examples included therein and to the Figures and their previous and following description.

It is to be understood that the terminology used herein is for the purpose of describing particular embodiments only and is not intended to limit the scope of the present invention which will be limited only by the appended claims.

It must be noted that as used herein and in the appended claims, the singular forms "a," "an," and "the" include plural references unless the context clearly dictates otherwise. Thus, for example, reference to a "fragment" can include one or more of such fragments, and so forth.

"Optional" or "optionally" means that the subsequently described event, circumstance, or material may or may not occur or be present, and that the description includes instances where the event, circumstance, or material occurs or is present and instances where it does not occur or is not present.

Ranges may be expressed herein as from "about" one particular value, and/or to "about" another particular value. When such a range is expressed, also specifically contemplated and considered disclosed is the range from the one particular value and/or to the other particular value unless the context specifically indicates otherwise. Similarly, when values are expressed as approximations, by use of the antecedent "about," it will be understood that the particular value forms another, specifically contemplated embodiment that should be considered disclosed unless the context specifically indicates otherwise. It will be further understood that the endpoints of each of the ranges are significant both in relation to the other endpoint, and independently of the other endpoint unless the context specifically indicates otherwise. Finally, it should be understood that all of the individual values and sub-ranges of values contained within an explicitly disclosed range are also specifically contemplated and should be considered disclosed unless the context specifically indicates otherwise. The foregoing applies regardless of whether in particular cases some or all of these embodiments are explicitly disclosed.

Optionally, in some aspects, when values or characteristics are approximated by use of the antecedents "about," "substantially," or "generally," it is contemplated that values within up to 15%, up to 10%, up to 5%, or up to 1% (above or below) of the particularly stated value or characteristic can be included within the scope of those aspects.

Optionally, in some aspects, when values or characteristics are approximated by use of the antecedents "about," "substantially," or "generally," in modifying geometric relationships such as perpendicular and parallel (e.g., "generally parallel") it is contemplated that values within up to 15 degrees, or within 10 degrees, or within 5 degrees, or within 1 degree of the particularly stated geometric relationship can be included within the scope of those aspects.

Unless defined otherwise, all technical and scientific terms used herein have the same meanings as commonly understood by one of skill in the art to which the disclosed apparatus, system, and method belong. Although any apparatus, systems, and methods and materials similar or equivalent to those described herein can be used in the practice or testing of the present apparatus, system, and method, the particularly useful methods, devices, systems, and materials are as described.

Throughout the description and claims of this specification, the word "comprise" and variations of the word, such as "comprising" and "comprises," means "including but not limited to," and is not intended to exclude, for example, other additives, components, integers or steps. In particular, in methods stated as comprising one or more steps or operations it is specifically contemplated that each step comprises what is listed (unless that step includes a limiting term such as "consisting of"), meaning that each step is not intended to exclude, for example, other additives, components, integers or steps that are not listed in the step.

As used herein, "insertional" can be understood to refer to an end or portion of a structure that, during use of the structure, is positioned away from or in a direction away from the clinician or the clinician's control device. Optionally, "insertional" can refer to a leading end or leading portion of a structure that is inserted into a patient.

Figure 3:
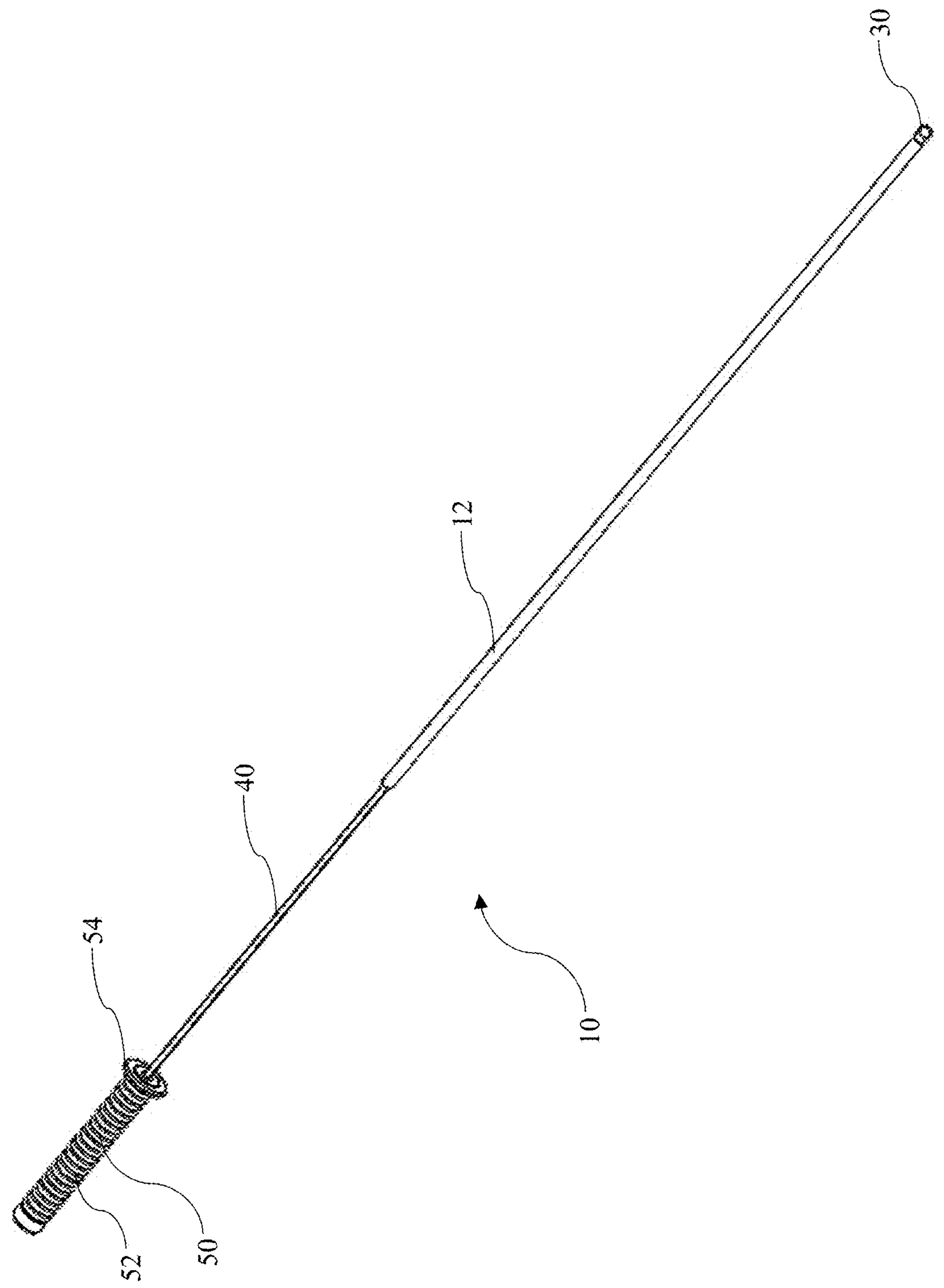
FIG. 3 is a perspective view of an exemplary apparatus for disrupting clots as disclosed herein, with the apparatus in an extended configuration.
Figure 4:
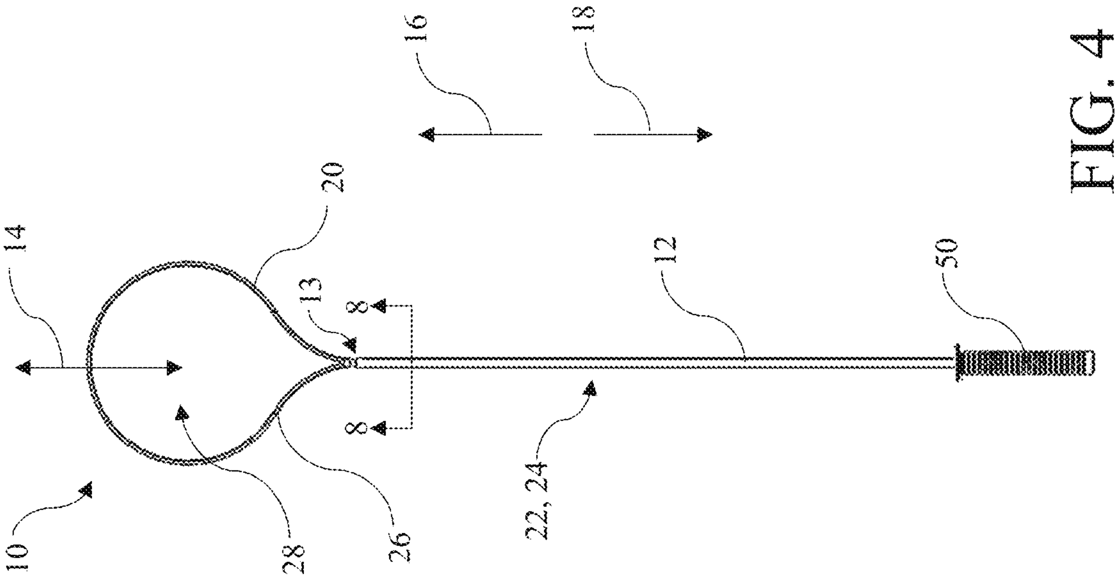
FIG. 4 is a side view of the apparatus of FIG. 3.
Figure 11B:
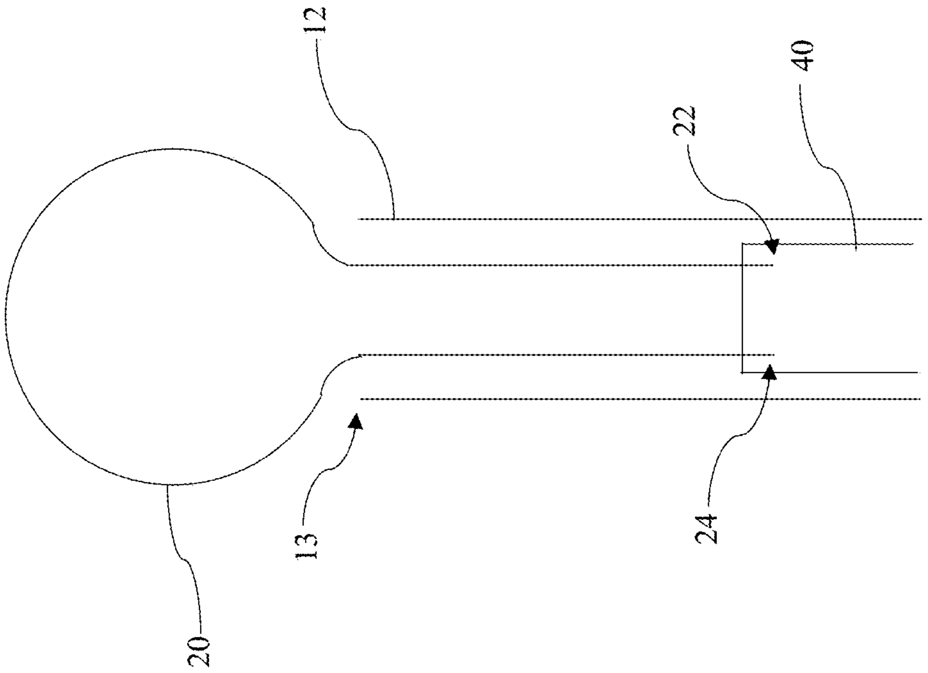
FIG. 11B shows a schematic view of the exemplary apparatus of FIG. 11A in a second position, with both ends of the wire retracted to form a loop having a second, reduced operational area.
Figure 11A:
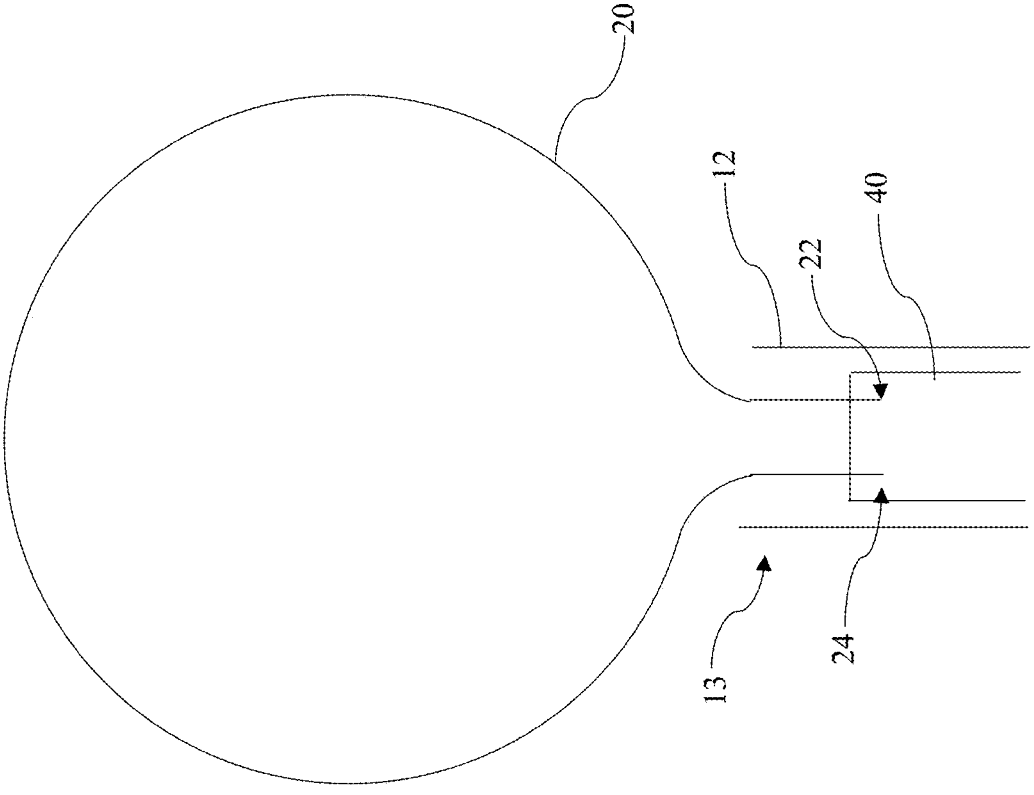
FIG. 11A shows a schematic view of an exemplary apparatus in a first position with the wire in a loop having a first operational area.
Figure 12B:
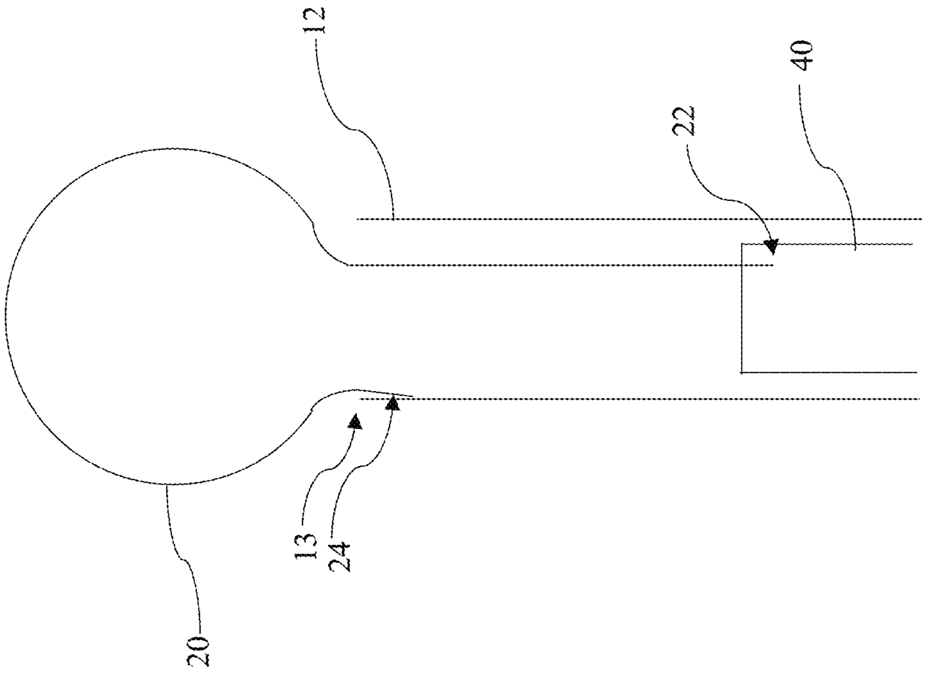
FIG. 12B shows a schematic view of the exemplary apparatus of FIG. 12A in a second position, with one end of the wire retracted to form a loop having a second, reduced operational area.
Figure 12A:
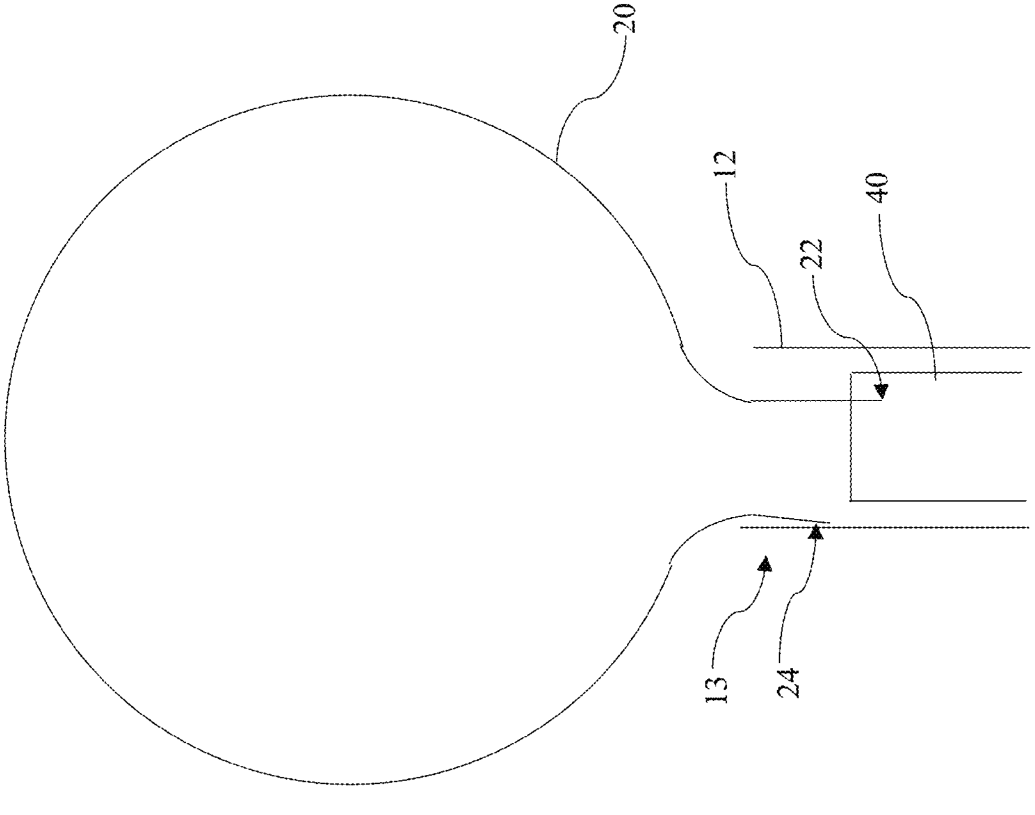
FIG. 12A shows a schematic view of an exemplary apparatus in a first position with the wire in a loop having a first operational area.

Disclosed herein, in various aspects, and with reference to FIGS. 1-5, is an apparatus 10 for disrupting clots (e.g., blood clots). The apparatus 10 can comprise an outer sleeve 12 having a longitudinal axis 14 and a first longitudinal end 13. Referring also to FIGS. 11A-12B, a wire 20 can have opposed first and second ends 22, 24. A portion of the wire 20 can form a wire loop 26 that extends from the opposed first and second ends 22, 24 in a first direction 16 along the longitudinal axis 14. As shown in FIG. 4, the wire loop 26 can surround an operational area 28. Retraction of one or both of the first and second ends 22, 24 of the wire 20 in a second direction 18 opposite the first direction 16 along the longitudinal axis 14 can decrease the operational area 28 of the wire loop 26. For example, in one aspect, and as shown in FIGS. 11A-11B, both the first and second ends 22, 24 can be coupled to a single structure (e.g., an inner body 40 as further disclosed herein) so that retraction of the single structure retracts the first and second ends. In another aspect, and as shown in FIGS. 12A-12B, only one of the first and second ends 22, 24 can be retracted, with the other of the first and second ends 22, 24 being fixed to the outer sleeve 12 (e.g., non-movably secured to an interior surface of the outer sleeve). Retraction of either a single end or both of the first and second ends 22, 24 can decrease the operational area 28 of the wire loop 26.

Figure 1:
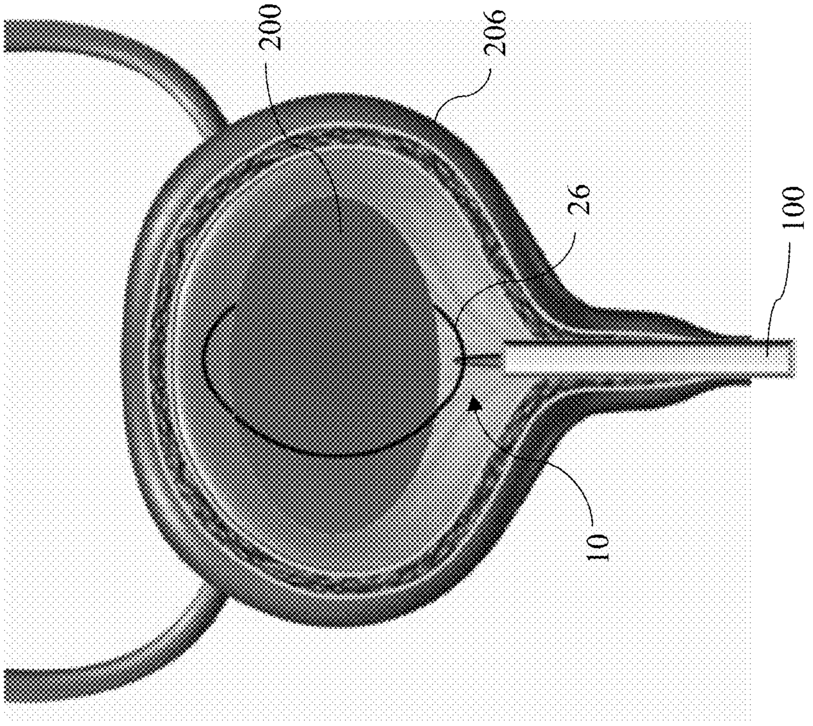
FIG. 1 is a schematic diagram of an apparatus for disrupting clots as disclosed herein, with the apparatus wrapped around a clot.

Accordingly, as illustrated in FIGS. 1-2, and as further disclosed herein, the apparatus can be configured to encircle portions of a clot (as shown in FIG. 1) and cut the clot into fragments (as shown in FIG. 2). The cutting process can be repeated as necessary until the clot fragments have dimensions small enough for removal.

Figure 6:
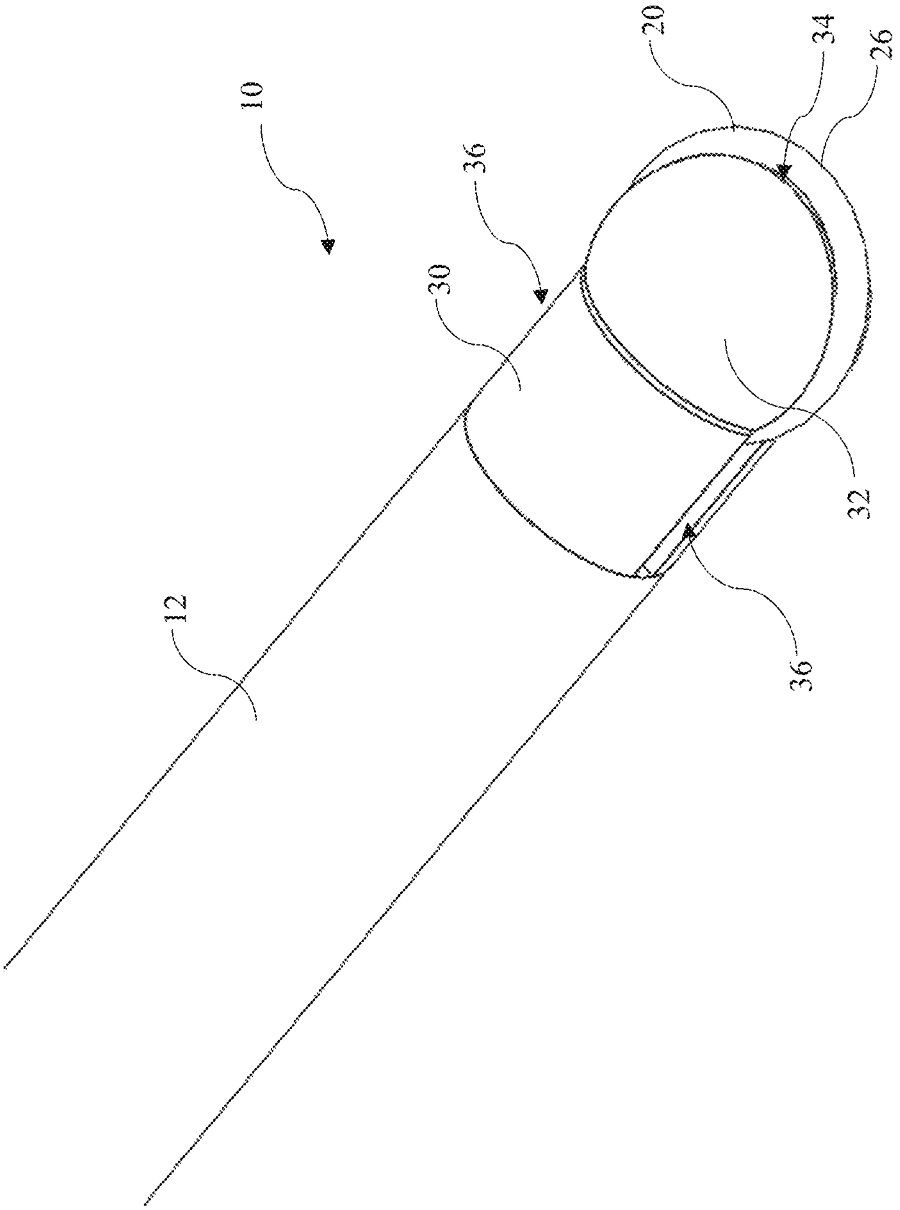
FIG. 6 is a partial perspective view of an insertional end of the apparatus of FIG. 3, with the apparatus in the retracted configuration.

Referring also to FIGS. 3 and 6, in some aspects, the apparatus 10 can comprise an insertional tip 30 that is coupled to the outer sleeve 12. The insertional tip 30 can have an outer surface 32. Optionally, a portion of the outer surface 32 of the insertional tip 30 can be rounded (e.g., spherical).

At least a portion of the insertional tip 30 can be disposed within the operational area of the wire loop. When in a fully retracted configuration, the wire loop can be configured to bias against the outer surface of the insertional tip. In this way, the insertional tip 30 can prevent the wire loop 26 from being pulled into the outer sleeve 12, thereby preventing the wire 20 from getting wrapped around itself, kinked, or otherwise caught in the outer sleeve. The insertional tip 30 can therefore promote cycling of the wire loop between extended and contracted configurations.

In further aspects, and as shown in FIG. 6, the outer surface 32 of the insertional tip 30 can define a groove 34 that is configured to receive a portion of the wire therein.

In further aspects, the insertional tip 30 can be integral to the outer sleeve 12. For example, the outer sleeve 12 can define two holes through which respective portions of the wire can extend, and the portion of the outer sleeve itself between the two holes can serve as a stop to prevent an entirety of the wire loop from being pulled into the outer sleeve 12.

The insertional tip 30 can further comprise side slots 36 that extend along the length of the apparatus 10 and permit the wire to extend therethrough. As shown in FIG. 6, the side slots 36 can optionally comprise two side slots positioned on opposing sides of the insertional tip such that each of the two side slots can concurrently receive portions of the wire.

Figure 5:
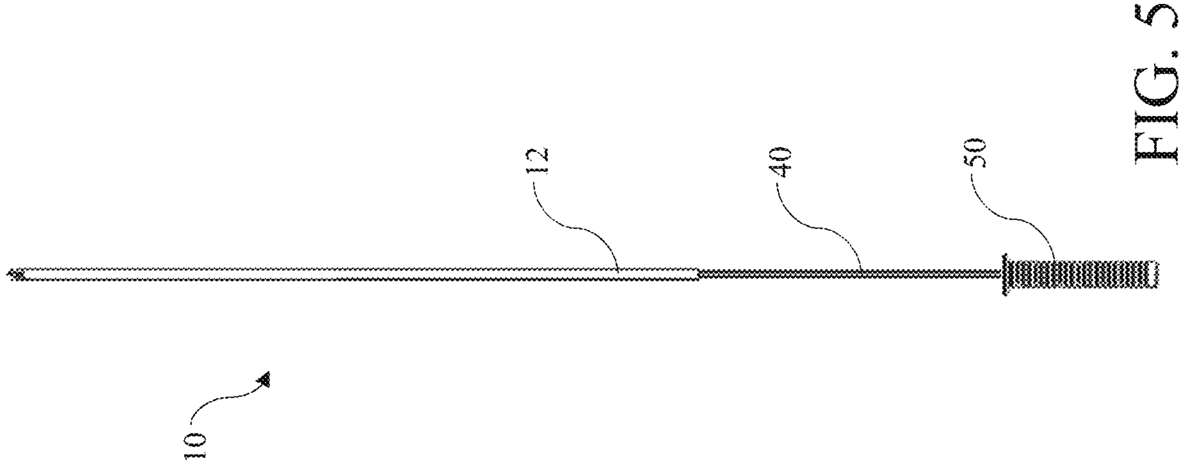
FIG. 5 is a side view of the apparatus of FIG. 3, with the apparatus in a retracted configuration.
Figure 8:
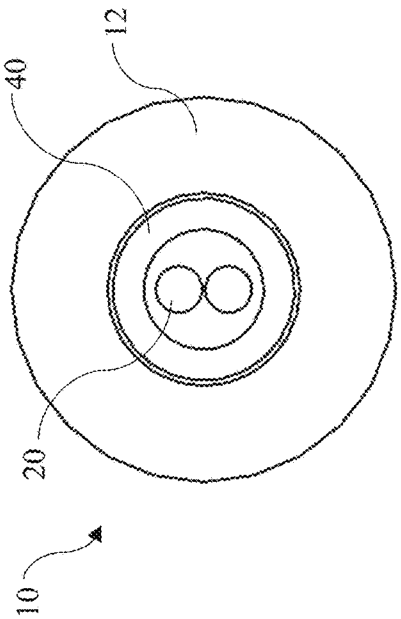
FIG. 8 is a cross sectional view of the apparatus of FIG. 3, taken in the plane 8-8 of FIG. 4.
Figure 7:
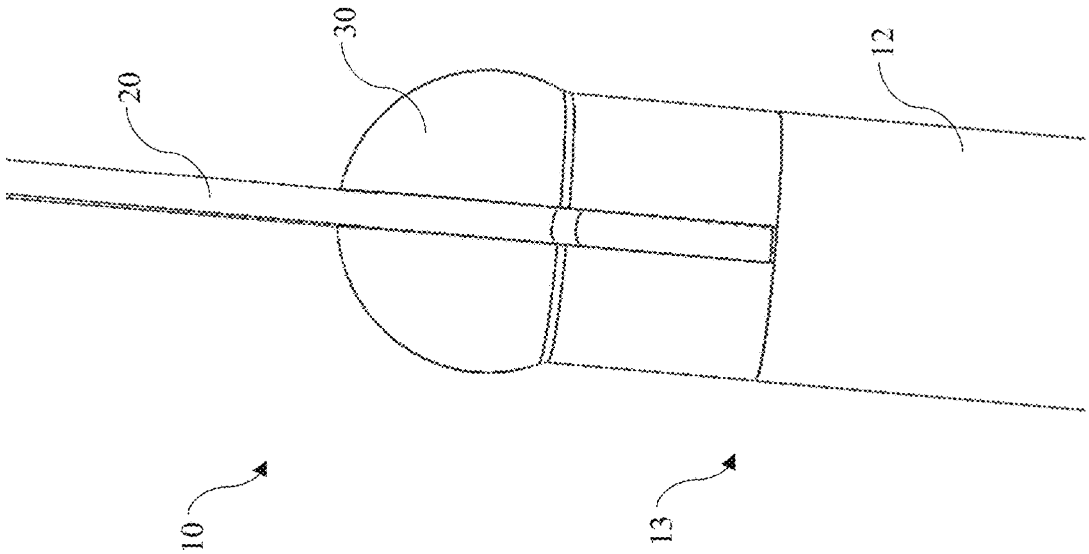
FIG. 7 is a partial perspective view of the insertional end of the apparatus of FIG. 3, with the apparatus in the extended configuration.
Figure 9B:
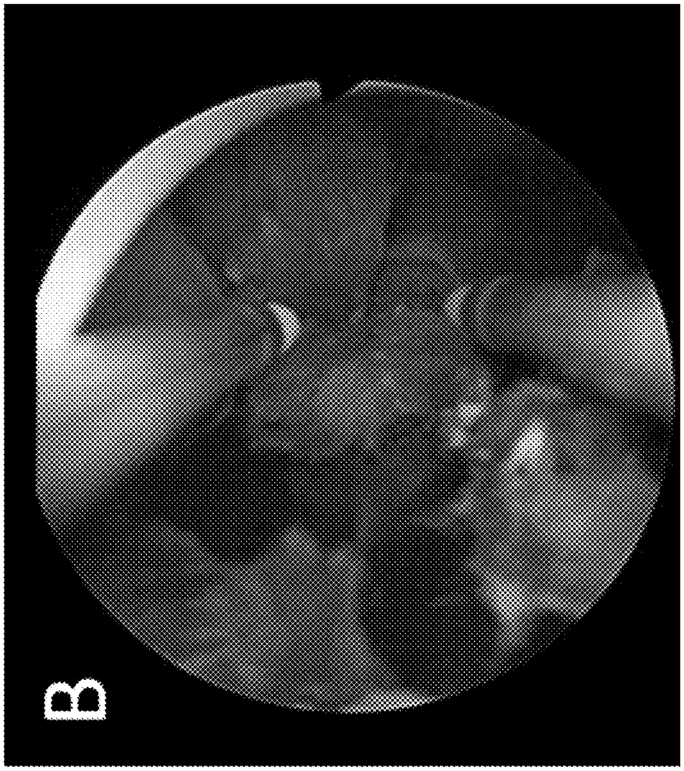
FIG. 9B is a view of the clot of FIG. 9A from a cystoscope.
Figure 9A:
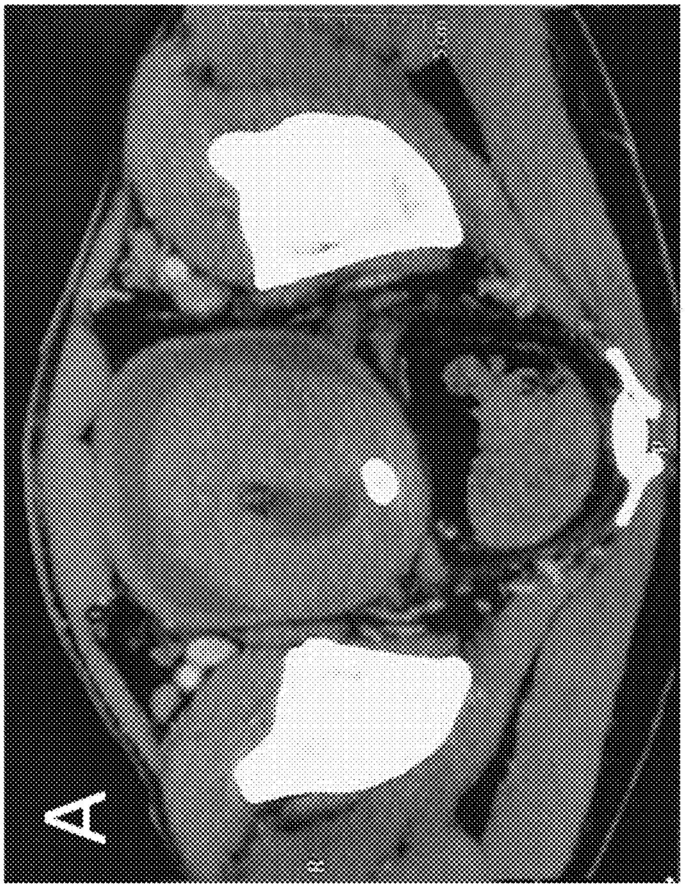
FIG. 9A is an ultrasound of a clot.

In some aspects, and with reference to FIGS. 5 and 8, the apparatus 10 can have an inner body 40 that is at least partially received within the outer sleeve 12. The inner body 40 can be slidable relative to the outer sleeve 12. Optionally, as shown in FIGS. 11A-11B, the first and second ends 22, 24 of the wire 20 can be coupled to the inner body 40 so that retraction of the inner body 40 relative to the outer sleeve 12 in the second direction 18 retracts both the first and second ends of the wire 20. Alternatively, in other aspects, and as shown in FIGS. 12A-12B, only one of the first or second ends 22, 24 of the wire 20 can be coupled to the inner body 40, with the other of the first or second ends coupled to an inner surface of the outer sleeve. In these aspects, it is contemplated that retraction of the inner body 40 in the second direction 18 can retract only one of the first or second ends of the wire. In both examples, it is contemplated that retraction of the inner body 40 can cause a reduction in the operational area and diameter of the wire loop.

The inner body 40 can optionally comprise stainless steel. The inner body 40 can be sufficiently rigid to endure cyclic and/or repeated movement through the outer sleeve 12. In some aspects, the inner body 40 can be cylindrical. The first and second ends 22, 24 of the wire 20 can be coupled to the inner body 40 via, for example, one or more fasteners and/or deformation of the inner body (e.g., crimping of the inner body) in a configuration in which the first and second ends are secured to the inner body.

Referring also to FIG. 8, illustrating a cross section of the apparatus 10, in some optional aspects, the inner body 40 can be an inner tube. Optionally, the first and second ends 22, 24 of the wire 20 can be positioned within the inner tube. In further aspects, the inner body 40 can be non-hollow. In these aspects, it is contemplated that the first and second ends 22, 24 of the wire 20 can be secured to an end of the inner body 40.

Optionally, the apparatus 10 can comprise a handle 50 that is coupled to the inner body 40. The handle 50 can have a gripping surface 52. Optionally, the gripping surface 52 can be a textured surface that is configured to promote grip. The textured surface can comprise ridges, knurls, a rough profile, finger grooves, combinations thereof, or any feature that promotes grip. Optionally, the handle 50 can define a radial flange 54 that is in the first direction 18 relative to the gripping surface. A user can push against the radial flange 54 to effect axial movement of the inner body 40 and opening of the wire loop 26.

In some aspects, the inner body 40 can be movable along the longitudinal axis 14 of the outer sleeve 12 from a first position in which the wire loop is in a fully retracted position within the outer sleeve (FIG. 5) to a second position (FIG. 4) that is axially translated or shifted by at least 10 cm, at least 12 cm, at least 14 cm, or at least 16 cm from the first position so that the wire loop extends outwardly beyond the outer sleeve. Accordingly, in exemplary embodiments, with the inner body in the second position, the wire loop 26 can extend outwardly from the outer sleeve 12 and have a diameter from about 6 cm to about 20 cm (e.g., about 10 cm), whereas with the inner body in the first position, the wire loop is more fully housed within the outer sleeve 12 (such that the wire loop has a minimum diameter and/or is fully received within the outer sleeve). In some aspects, during deployment of the wire loop, the handle 50 can engage the outer sleeve 12 to stop further insertional movement of the wire loop.

Figure 10B:
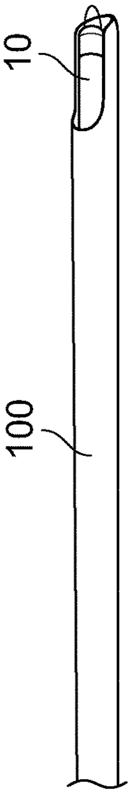
FIG. 10B is a partial view of the insertional end of the apparatus of FIG. 10A.
Figure 10A:
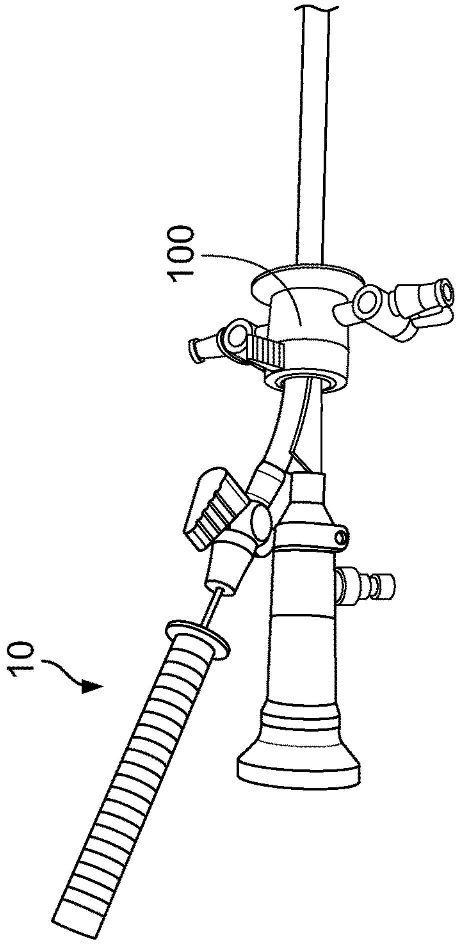
FIG. 10A is a partial view of an exemplary apparatus for disrupting clots as disclosed herein, with the apparatus shown inserted into a working port of a cystoscope.

The outer sleeve 12 can have a major transverse dimension (e.g., a diameter) in cross sectional planes perpendicular to the longitudinal axis 14. In some aspects, the major transverse dimension is ⅛ inch or less. In various optional aspects, the outer sleeve 14 can have a major transverse dimension (e.g., major diameter) from about 1/16 inch to about ⅛ inch, or from about 4 mm to about 5 mm. Accordingly, the outer sleeve 14 can be configured for receipt into a cystoscope 100, as illustrated in FIG. 10A.

In some optional aspects, the outer sleeve 12 can have a length from about 14 inches to about 18 inches along the longitudinal axis 12. In other aspects, the outer sleeve 12 can have a length from about 10 to about 20 inches, or about 15.7 inches (40 mm).

In some optional aspects, the wire 20 can comprise a nickel titanium alloy (e.g., nitinol). In further aspects, it is contemplated that the wire 20 can comprise a high-memory biocompatible material having sufficient rigidity for operation. For example, the wire can have sufficient rigidity to remain generally in the same position when the wire loop 26 fully extends from the outer sleeve, regardless of the orientation of the apparatus 10. In various aspects, the wire 20 can have a thickness from about 0.01 inches to about 0.02 inches (e.g., 0.015 inches). In further aspects, the wire can have a thickness from about 0.03 inches to about 0.10 inches, or from about 0.04 inches to 0.07 inches, or about 0.059 inches. Such a thickness can make the wire suitable for maintaining its rigidity as it is manipulated within a portion of the body (e.g., within a bladder) and around a clot.

In exemplary aspects, the outer sleeve 12 can comprise polymer (e.g., polyoxymethylene, such as DELRIN polymer). It should be understood that materials described herein are provided as exemplary materials that can be suitable, while other materials may be substituted based on factors such as availability and cost.

Each of the outer sleeve 12 and the inner body 40 can be rigid or sufficiently rigid such that they do not significantly bend. In this way, the outer sleeve and the inner body can be easily advanced into the cystoscope 100 and can be robust for repeated actuation during use.

In some aspects, the apparatus 10 can have only one single wire loop 26. It is contemplated that the single wire loop 26 can be optimal for selected placement of said loop around the clot. However, in further aspects, the apparatus 10 can comprise two or more wire loops. For example, the apparatus 10 can comprise from one to six wire loops (e.g., four wire loops). Optionally, in some aspects, each of the wire loops can extend from respective first and second ends of a corresponding wire, with the first and second ends of each of said corresponding wires being coupled to the inner body 40.

As illustrated, it is contemplated that when the wire loop 26 is opened (FIGS. 1 and 4), the open area 28 within the wire loop 26 can be planar or generally planar, and the longitudinal axis of the outer sleeve can be co-planar or parallel to or generally co-planar or generally parallel to the open area 28. For example, the longitudinal axis 14 of the outer sleeve 12 can be coplanar with the open area 28 of the wire loop 26. That is, the open area 28 can include a portion of the longitudinal axis 14. In this way, controlled movement of the apparatus (including the outer sleeve) can allow the wire loop 26 to be effectively positioned around the clot.

In some optional aspects, the apparatus 10, or components thereof, can be sterilizable or autoclavable. In other aspects, the apparatus 10, or components thereof, can be disposable (for example, as a single-use apparatus and/or component).

Method of Use

Referring to FIGS. 1-2 and 10A-B, a method of disrupting a blood clot 200 in a patient can include inserting at least a portion of the apparatus 10 into a cystoscope 100. The wire loop 26 can be advanced in an insertional direction to an open position, at which point the wire loop can be positioned around a portion of the blood clot. One or both of the first and second ends of the wire can be retracted to draw the wire loop through the blood clot (optionally, cooperating with the insertional tip 30) to divide the blood clot into at least a first piece 202 and a separated second piece 204 (collectively, fragments). For example, a clinician can manually pull on the handle relative to the outer sleeve 12 to retract the inner body 40.

The process can be repeated to iteratively section the blood clot and its generated fragments into smaller and smaller pieces. For example, the wire loop can be positioned around the first piece of the blood clot, one or both of the first and second ends of the wire can be retracted to draw the wire through the first portion of the blood clot to divide the blood clot into at least a first sub-piece and a separated second sub-piece. The opening and closing of the wire loop 26 (that is, the increasing and decreasing of its operational area 28) can be done manually. That is, the clinician can push and pull the handle relative to the outer sleeve 12 to cause the opening and closing of the wire loop. In this way, the clinician can provide a sufficient but controlled force. Thus, the clinician can use tactile feedback to prevent injury from occurring during cycling the loop about and between extended and contracted configurations.

In this way, the blood clot 200 can be reduced into pieces/fragments that can be removed from the body. For example, the first and second pieces 202, 204 of the blood clot 200, or fragments thereof, can be suctioned out of a bladder 206. In exemplary aspects, a cystoscopic suctioning device such as, but not limited to an ELLIK bladder evacuator, can be used to remove said fragments.

The disclosed apparatus and method have major advantages over current suction-based disruption treatment options for blood clots in the bladder. One advantage is that the disclosed apparatus can disrupt the clot far more rapidly than conventional methods. This can significantly decrease operative time. Other advantages include that the disclosed apparatus can allow for the clot to be disrupted under direct vision and eliminates the requirement for prolonged high-pressure suctioning to remove the clot. This can significantly improve safety of clot evacuation and decreases the risk of bladder injury.

Exemplary Aspects

In view of the described products, systems, and methods and variations thereof, herein below are described certain more particularly described aspects of the invention. These particularly recited aspects should not however be interpreted to have any limiting effect on any different claims containing different or more general teachings described herein, or that the "particular" aspects are somehow limited in some way other than the inherent meanings of the language literally used therein.

Aspect 1: An apparatus comprising:

an outer sleeve having a longitudinal axis and a first longitudinal end; and a wire having opposed first and second ends, wherein a portion of the wire forms a wire loop that extends from the opposed first and second ends in a first direction along the longitudinal axis and outwardly from the first longitudinal end of the outer sleeve, wherein the wire loop surrounds an operational area, wherein retraction of at least one of the first and second ends of the wire in a second direction opposite the first direction along the longitudinal axis decreases the operational area of the wire loop.

Aspect 2: The apparatus of aspect 1, further comprising an insertional tip that is coupled to the outer sleeve, wherein the insertional tip has an outer surface, wherein at least a portion of the insertional tip is disposed within the operational area of the wire loop, wherein, when in a fully retracted configuration, the wire loop is configured to bias against the outer surface of the insertional tip.

Aspect 3: The apparatus of aspect 2, wherein the outer surface of the insertional tip defines a groove that is configured to receive a portion of the wire therein.

Aspect 4: The apparatus of aspect 2 or aspect 3, wherein a portion of the outer surface of the insertional tip is spherical.

Aspect 5: The apparatus of any one of the preceding aspects, further comprising an inner body that is at least partially received within the outer sleeve, wherein the inner body is slidable relative to the outer sleeve, wherein the first and second ends of the wire are coupled to the inner body so that retraction of the inner body relative to the outer sleeve in the second direction retracts both the first and second ends of the wire.

Aspect 6: The apparatus of aspect 5, wherein the inner body is an inner tube, wherein the first and second ends of the wire are positioned within the inner tube.

Aspect 7: The apparatus of aspect 5 or aspect 6, wherein the apparatus comprises a handle that is coupled to the inner body.

Aspect 8: The apparatus of any one of aspects 5-7, further comprising an insertional tip that is coupled to the outer sleeve, wherein the insertional tip has an outer surface, wherein at least a portion of the insertional tip is disposed within the operational area of the wire loop, wherein, when in a fully retracted configuration, the wire loop is configured to bias against the outer surface of the insertional tip, wherein the inner body is movable along the longitudinal axis of the outer sleeve from a first position in which the wire loop is in a fully retracted position to a second position in which the inner body is at least 10 cm from the first position in an insertional direction relative to the outer sleeve.

Aspect 9: The apparatus of any one of the preceding aspects, wherein the outer sleeve has a major transverse dimension, wherein the major transverse dimension is ⅛ inch or less.

Aspect 10: The apparatus of aspect 9, wherein the major transverse dimension is from about 4 mm to about 5 mm.

Aspect 11: The apparatus of aspect 9 or aspect 10, wherein the major transverse dimension is a diameter.

Aspect 12: The apparatus of any one of the preceding aspects, wherein the outer sleeve has a length from about 14 inches to about 18 inches along the longitudinal axis.

Aspect 13: The apparatus of aspect 12, wherein the length of the outer sleeve is about 40 cm.

Aspect 14: The apparatus of any one of the preceding aspects, wherein the wire comprises a nickel titanium alloy.

Aspect 15: The apparatus of any one of the preceding aspects, wherein the wire has a thickness from about 0.01 inches to about 0.02 inches.

Aspect 16: The apparatus of aspect 15, wherein the wire has a thickness of about 0.015 inches.

Aspect 17: A method of disrupting a blood clot in a patient, the method comprising:

inserting at least a portion of the apparatus as in any one of the preceding aspects into a cystoscope;

advancing the wire in an insertional direction to deploy the wire loop outwardly beyond the outer sleeve;

positioning the wire loop around a portion of the blood clot; and retracting one or both of the first and second ends of the wire to draw the wire through the blood clot to divide the blood clot into at least a first piece and a separated second piece.

Aspect 18: The method of aspect 17, further comprising:
positioning the wire loop around the first piece of the blood clot; and
retracting one or both of the first and second ends of the wire to draw the wire through the first piece of the blood clot to divide the blood clot into at least a first sub-piece and a separated second sub-piece.

Aspect 19: The method of aspect 17 or aspect 18, further comprising removing at least one of the first or separated second pieces from the patient.

Aspect 20: The method of aspect 19, wherein the at least one of the first or separated second pieces is removed from the patient via suction.

Those skilled in the art will recognize, or be able to ascertain using no more than routine experimentation, many equivalents to the specific embodiments of the method and compositions described herein. Such equivalents are intended to be encompassed by the following claims.

What is claimed is:

1. An apparatus comprising:
an outer sleeve having a longitudinal axis and a first longitudinal end;
a wire having opposed first and second ends, wherein a portion of the wire forms a wire loop that extends from the opposed first and second ends in a first direction along the longitudinal axis and outwardly from the first longitudinal end of the outer sleeve, wherein the wire loop surrounds an operational area, wherein retraction of at least one of the first and second ends of the wire in a second direction opposite the first direction along the longitudinal axis decreases the operational area of the wire loop;
an inner body that is at least partially received within the outer sleeve, wherein the inner body is slidable relative to the outer sleeve by an axial distance of at least 10 cm, wherein the first and second ends of the wire are coupled to the inner body so that retraction of the inner body relative to the outer sleeve in the second direction retracts both the first and second ends of the wire, and wherein the operational area of the wire loop is configured to progressively change during sliding movement of the inner body relative to the outer sleeve along an entirety of the axial distance of at least 10 cm; and
an insertional tip that is coupled to the outer sleeve, wherein the insertional tip has an outer surface, wherein at least a portion of the insertional tip is disposed within the operational area of the wire loop, wherein, when in a fully retracted configuration, the wire loop is configured to bias against the outer surface of the insertional tip.

2. The apparatus of claim 1, wherein the outer surface of the insertional tip defines a groove that is configured to receive a portion of the wire therein.

3. The apparatus of claim 1, wherein a portion of the outer surface of the insertional tip is spherical.

4. The apparatus of claim 1, wherein the inner body is an inner tube, wherein the first and second ends of the wire are positioned within the inner tube.

5. The apparatus of claim 1, wherein the apparatus comprises a handle that is coupled to the inner body, wherein the wire loop is movable about and between the fully retracted configuration and a fully deployed configuration, wherein the handle and the outer sleeve cooperate to form a stop that is configured to inhibit distal movement of the wire loop beyond the outer sleeve when the wire loop is in the fully deployed configuration, and wherein the operational area of the wire loop is configured to progressively change during sliding movement from the fully retracted configuration to the fully deployed configuration.

6. The apparatus of claim 1, wherein the outer sleeve has a major transverse dimension, wherein the major transverse dimension is ⅛ inch or less.

7. The apparatus of claim 6, wherein the major transverse dimension is from about 4 mm to about 5 mm.

8. The apparatus of claim 6, wherein the major transverse dimension is a diameter.

9. The apparatus of claim 1, wherein the outer sleeve has a length from about 14 inches to about 18 inches along the longitudinal axis.

10. The apparatus of claim 1, wherein the wire comprises a nickel titanium alloy.

11. The apparatus of claim 1, wherein the wire has a thickness from about 0.01 inches to about 0.02 inches.

12. The apparatus of claim 11, wherein the wire has a thickness of about 0.015 inches.

13. The apparatus of claim 1, wherein the inner body is moveable to a position in which the operational area surrounded by the wire loop has a diameter from about 6 cm to about 20 cm.

14. The apparatus of claim 1, wherein, in a deployed configuration, the wire loop has a first side and a second side that are spaced along a transverse axis that is perpendicular to the longitudinal axis, wherein the wire loop has a distal end portion extending between the first side and the second side, and wherein the distal end portion extends continuously from the first side to the second side along an arcuate path.

15. A method of disrupting a blood clot in a patient, the method comprising:
inserting, into a cystoscope, at least a portion of an apparatus comprising:
an outer sleeve having a longitudinal axis and a first longitudinal end;
a wire having opposed first and second ends, wherein a portion of the wire forms a wire loop that extends from the opposed first and second ends in a first direction along the longitudinal axis and outwardly from the first longitudinal end of the outer sleeve, wherein the wire loop surrounds an operational area, wherein retraction of at least one of the first and second ends of the wire in a second direction opposite the first direction along the longitudinal axis decreases the operational area of the wire loop; and
an insertional tip that is coupled to the outer sleeve, wherein the insertional tip has an outer surface, wherein at least a portion of the insertional tip is disposed within the operational area of the wire loop, wherein, when in a fully retracted configuration, the wire loop is configured to bias against the outer surface of the insertional tip;
advancing the wire in an insertional direction to deploy the wire loop outwardly beyond the outer sleeve;
positioning the wire loop around a portion of the blood clot; and
retracting one or both of the first and second ends of the wire to draw the wire through the blood clot to divide the blood clot into at least a first piece and a separated second piece.

16. The method of claim 15, further comprising:
positioning the wire loop around the first piece of the blood clot; and
retracting one or both of the first and second ends of the wire to draw the wire through the first piece of the blood clot to divide the blood clot into at least a first sub-piece and a separated second sub-piece.

17. The method of claim 15, further comprising removing at least one of the first or separated second pieces from the patient.

18. The method of claim 17, wherein the at least one of the first or separated second pieces is removed from the patient via suction.

* * * * *